(12) United States Patent
Kreis et al.

(10) Patent No.: US 7,445,753 B1
(45) Date of Patent: Nov. 4, 2008

(54) AUTOMATED AMPOULE BREAKING DEVICE

(75) Inventors: Richard J. Kreis, Bel Air, MD (US); Robert J. Pazda, Kingsville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 231 days.

(21) Appl. No.: 11/398,729

(22) Filed: Mar. 28, 2006

(51) Int. Cl.
*B01L 3/00* (2006.01)

(52) U.S. Cl. ....................................................... 422/99
(58) Field of Classification Search .................... 422/99
See application file for complete search history.

(56) References Cited

U.S. PATENT DOCUMENTS 6,228,657 B1 * 5/2001 Genovese et al. ........... 436/167

* cited by examiner

*Primary Examiner*—Walter D Griffin
*Assistant Examiner*—Bobby Ramdhanie
(74) *Attorney, Agent, or Firm*—Ulysses John Biffoni (57) ABSTRACT

An automated ampoule breaking device includes a carriage having an opening for receiving and securely retaining a substrate in a substantially upright position, wherein the substrate includes at least one flexible compartment each having an outlet at the lower end and at least one ampoule contained therein; and at least one movable projection operatively associated with the carriage, wherein each of the at least one projection adapted for applying sufficient pressure progressing from the upper to the lower end of the corresponding flexible compartment to crush the at least one ampoule and direct the contents of the crushed ampoule out of the respective flexible compartment through the outlet.

13 Claims, 6 Drawing Sheets

AUTOMATED AMPOULE BREAKING DEVICE

GOVERNMENT INTEREST

The invention described herein may be manufactured, used and licensed by or for the U.S. Government.

FIELD OF THE INVENTION

The present invention relates to devices for breaking ampoules, and more particularly to an automated ampoule breaking device for releasing contents of one or more ampoules at appropriate time intervals in a predetermined sequence.

BACKGROUND OF THE INVENTION

Generally, an ampoule is a vial-like container hermetically sealed to hold substances that may be sensitive to the external environment or ambient air. The ampoule may be formed from glass or plastic materials suitable for preserving the hermetic seal over an extended time period. For glass ampoules, the ampoule is typically sealed by melting the thin top usually with a blowtorch flame after filling, and most commonly used as a container for perishable products such as pharmaceuticals. Some ampoules are designed with a score mark around the neck so that the sealed top may be simply snapped off by hand; while others are pre-packaged in a flexible outer container, which may optionally contain a secondary substance. In the latter form, the user can safely break the ampoule(s) within the flexible container. The contents of the broken ampoule are then released into the flexible outer container for dispensing.

In biological or chemical detection systems, testing reagents are used for detecting the presence of compounds in samples. To ensure reliability and minimize false results, a sufficient amount of testing reagents are need to properly react with the sample. Glass ampoules have been used in field testing scenarios to portably hold chemical testing reagents in pre-measured amounts. Such ampoules are effective in maintaining a hermetic seal to prevent contamination by the environment prior to testing, and can be cleanly broken to release the reagents in the amounts needed without measuring during the chemical test. They are particularly efficient for their portability, ease of use and flexible storage capabilities and advantageous for use in field testing operations, particularly where test users are typically required to wear cumbersome protective gear in a potentially hazardous environment.

The M256 series of chemical agent detector kits including the M256 and M256A1, utilizes glass ampoules for storing and dispensing chemical testing agents to test the presence of noxious and toxic chemicals. These kits are available from manufacturers Truetech Inc. of Riverhead, N.Y. and Anachemia Chemicals Inc. of Rouses Point, N.Y. The kits are manually operated and form an essential element in chemical warfare agent defensive measures for personnel. The kits are used to detect hazardous concentrations of blood agents (e.g., hydrogen cyanide, cyanogens chloride), nerve (e.g., G-class and V-class), and blister agents (e.g., mustard, phosgene oxime) in both vapor and liquid form. In this manner, the kits can be used to indicate to the user whether it is safe to remove the protective mask, or as a confirmatory test after a chemical agent alarm has sounded.

The M256 has two primary test components: the vapor-sampler and M8 detection paper. The components are designed to allow the user in full protective gear to perform the chemical agent tests. All the chemical test reagents needed to test the vapors and aerosols are stored within ampoules contained in the vapor-sampler's body. The M8 detection paper is specifically designed to provide a testing surface to support the reaction between the chemical testing reagents and the chemical agents including toxic blood, nerve, and blister agents in liquid, aerosol or vapor form, and produce a uniquely colored response. The colored response indicates to the user whether a chemical warfare agent is present.

Although the M256 kits provide an affordable, reliable and prompt chemical detector, they are costly and very labor intensive to implement and also prone to human errors due to the conditions under which the tests are implemented. To minimize such errors, it is normally recommended that two users conduct the kit test; one manually performs the chemical testing, while the other reads the instructions for the test kit to the first user. Generally, the users must follow detailed and precise instructions with multiple steps involving many physical and mechanical manipulations performed in a set chronological timed sequence. With the protective gear the users are typically wearing, the users' ability to perform the tasks is severely reduced. Collectively, these factors significantly encumber the users' ability to perform any chemical detection task. Typically, hazardous material teams have highly trained but limited personnel resources, which can be consumed to perform the operations required by the M256 chemical agent detector kit.

A prior art chemical testing device having a testing surface is disclosed in U.S. Pat. No. 6,228,657 issued to Genovese et al. The device taught by Genovese et al. includes a crushing mechanism for breaking ampoules containing chemical testing reagents attached to a collector element similar to the vapor-sampler's body of the M256. The crushing mechanism includes a movable spring or solenoid powered member adapted for shattering the ampoule to release the chemical testing reagents through a channel onto the testing surface. In some instances, the crushing mechanism is unable to release the chemical testing reagents when the ampoule is only partially broken, or when a portion of the ampoule retains all, if not, most of the reagent and prevents the reagent from flowing freely down the channel. Moreover, the device still requires the users to manually perform many physical and mechanical manipulations in a set chronological timed sequence.

Accordingly, there is a need for an automated ampoule breaking device designed to effectively break ampoules at an appropriate time interval in a predetermined sequence during the implementation of chemical or biological detection testing, while directing the flow of the contents of the broken ampoules onto a testing surface in an automated manner. There is a further need for an automated ampoule breaking device capable of greatly simplifying operating procedures in testing for the presence of hazardous materials such as chemical and/or biological agents in the field in a manner that enhances reliability and reproducibility, while reducing the complexity, the labor and the costs associated with such tests.

SUMMARY OF THE INVENTION

The present invention relates generally to an automated ampoule breaking device useful for enhancing the breaking of ampoules and reliably emptying the contents of the broken ampoules onto a targeted area. The ampoules may contain flowable reagents for implementing biological and chemical testing. The automated ampoule breaking device of the present invention effectively increases the capability of currently available methods for implementing field testing of chemical and biological agents, while reducing personnel requirements and costs typically associated with such methods. The automated ampoule breaking device of the present invention is compact, portable and modular for easy assembly and operation in a short period of time. The present invention reduces the cost, time and labor associated with monitoring and detecting compounds of interest and expanding the detection capability of the corresponding system in a simple and effective manner, while maintaining high levels of accuracy, reliability and reproducibility.

In general, the automated ampoule breaking device of the present invention includes a carriage for receiving and retaining a substrate having one or more ampoules enclosed in flexible compartments, and at least one ampoule breaking mechanisms that is adapted to selectively break the ampoules at an appropriate time in a predetermined sequence, and thereafter actively emptying the contents of the broken ampoules from the flexible compartment. The automated ampoule breaking device of the present invention may further include a programmable microprocessor for initiating the breaking of the ampoules in a sequential manner at appropriate times.

In one aspect of the present invention, there is provided an automated ampoule breaking device, the device comprising:

a carriage having an opening for receiving and securely retaining a substrate in a substantially upright position, said substrate including at least one flexible compartment each having an outlet at the lower end and at least one ampoule contained therein; and at least one movable projection operatively associated with the carriage, each of said at least one projection adapted for applying sufficient pressure progressing from the upper to the lower end of the corresponding flexible compartment to crush the at least one ampoule and direct the contents of the crushed ampoule out of the respective flexible compartment through the outlet.

In another aspect of the present invention, there is provided a method for automating the breaking of ampoules, the method comprising the steps of:

assembling a plurality of ampoules each retained in flexible compartments on a card;

providing a plurality of test surfaces on said card;

providing fluid pathways from each flexible compartment to a selected one of said plurality of test surfaces; and automatically selectively rotating a cam head against one or more of said flexible compartments, at predetermined times to crush said ampoules; and directing the contents of the ampoules from the flexible compartments through an associated fluid pathway to an associated test surface.

BRIEF DESCRIPTION OF THE DRAWINGS

The following drawings, wherein like items may have the same reference designations, are illustrative of embodiments of the present invention and are not intended to limit the invention as encompassed by the claims forming part of the application.

DETAILED DESCRIPTION OF THE INVENTION

The present invention is directed to an automated ampoule breaking device for breaking one or more ampoules at appropriate times in a predetermined sequence, and ensuring that the content of the broken ampoule is directed to the corresponding target area. In particular, the automated ampoule breaking device is designed to enhance the performance and capability of chemical detection systems including, but not limited to, those using a form of collection elements or substrates containing ampoules referred herein as the Environmental Material Tickets (EMT) (e.g., vapor sampler of the M256).

The automated ampoule breaking device of the present invention ensures that the ampoules containing chemical testing reagents in the form of a flowable substance including liquids and solid particles, are properly broken at appropriate time intervals in a predetermined sequence, and the reagents are then urged from the broken ampoules to the proper testing surfaces as required by the particular chemical detection system. In this manner, the present invention operates to extend the detection capability and reliability of such chemical detection systems, while reducing the complexity, the manual labor and the costs needed to implement such systems, and increasing accuracy, precision and repeatability of results flowing therefrom.

The device of the present invention is designed to specifically minimize or eliminate the problems and limitations associated with manual implementation of the ampoule-based tests by human users or operators where the user is expected to conduct the test while in protective clothing that restricts physical movement. This includes, for example, wearing protective face masks which can impair the user's field of vision and acuity, and wearing bulky chemical resistant gloves which can limit the user's finger dexterity and strength. These and other limitations can adversely affect the user's ability to break the glass ampoules and manipulate the ampoule contents. These difficulties are further compounded by the constant presence of elevated mental and physical stress coupled with working in a chemically contaminated emergency environment.

In one embodiment of the present invention, there is provided an automated ampoule breaking device that comprises a carriage having an opening for receiving and securely retaining a substrate in a substantially upright position, wherein the substrate includes at least one flexible compartment each having an outlet at the lower end and at least one ampoule contained therein; and at least one movable projection operatively associated with the carriage, wherein each of the at least one projection is adapted for applying sufficient pressure progressing from the upper to the lower end of the corresponding flexible compartment to crush the at least one ampoule and direct the contents of the crushed ampoule out of the respective flexible compartment through the outlet.

Figure 1:
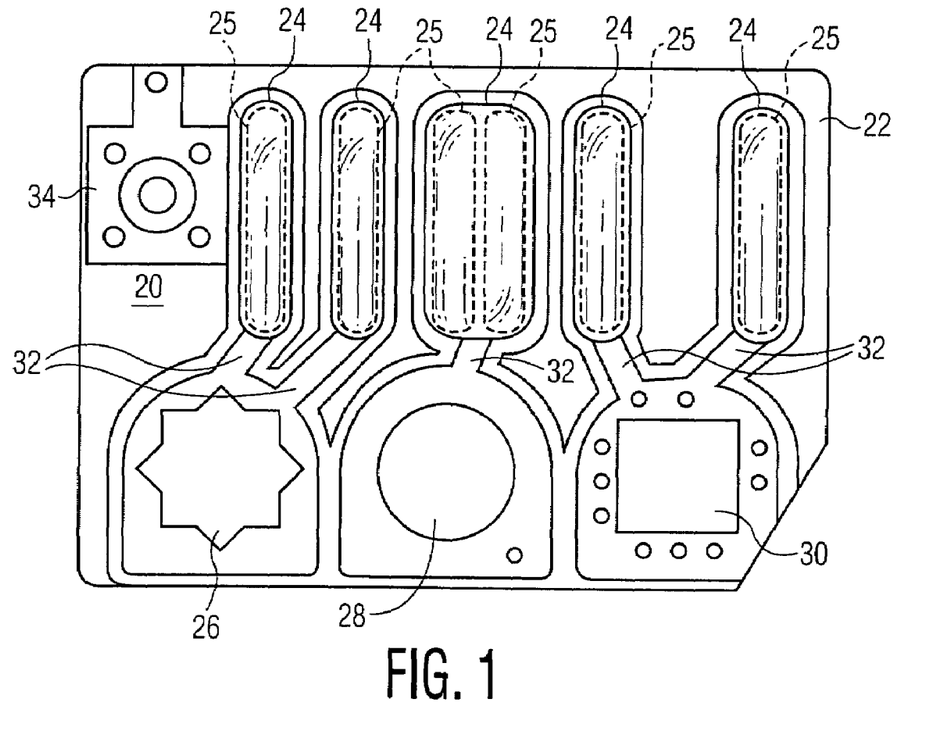
FIG. 1 is a front elevation view of a substrate having flexible compartments containing glass ampoules in accordance with the present invention.

Referring to FIG. 1, an Environmental Material Ticket (EMT) in the form of a vapor sampler from the M256 chemical agent detector kit is shown and identified generally by reference numeral 20. The EMT 20 is used to test vapor and aerosol samples for the presence of nerve agents, blood agents, and blister agents. It is the primary testing device in the M256 kit. Each issued kit includes twelve EMTs 20 individually sealed in a plastic laminated foil envelope. Once used, the EMT 20 is discarded. The EMT 20 generally includes a substrate 22 having five fluidly sealed flexible compartments 24, three test surfaces 26, 28, and 30, and fluid channels or ducts 32, all of which are molded into the substrate 22. The flexible compartment 24 is adapted to collapse when sufficient force is applied thereon. The fluid channels 32 provide a fluid connection between the flexible compartments 24 and the corresponding test surfaces 26, 28, and 30.

The EMT 20 further includes six glass ampoules 25 securely enclosed in the flexible compartments 24, and optionally a lewisite tablet rubbing tab 34 and tablet (not shown). The glass ampoules 25 each contain chemical testing reagents that react in a predictable manner with the vapor or aerosol forms of chemical warfare agents including nerve, blood and blister agents. The test surfaces 26, 28, and 30 are suitably located on the substrate 22 to minimize cross-contamination and ensure that each are suitably exposed to the suspect vapor. To assist the user in identifying the test conducted, each test surface 26, 28, and 30 is shaped differently.

To implement the test, the glass ampoules 25 contained in the corresponding flexible compartments 24 are broken at the appropriate times in a predetermined chronological sequence. The reagents released from the broken glass ampoules 25 are urged through the corresponding channels 32 and onto the respective test surface 26, 28 or 30 by squeezing the flexible compartment 24. Once the reagents reach the test surface 26, 28 or 30, they can react with the sample contained thereon. In order to obtain reliable test results, the chemical test reagents should be released in amounts sufficient to substantially saturate the test surfaces 26, 28 and 30. Further details about the EMT 20 can be found in U.S. Pat. No. 6,228,657, the content of which is incorporated herein by reference to the extent that it does not conflict with the teachings of the present invention.

Figure 2:
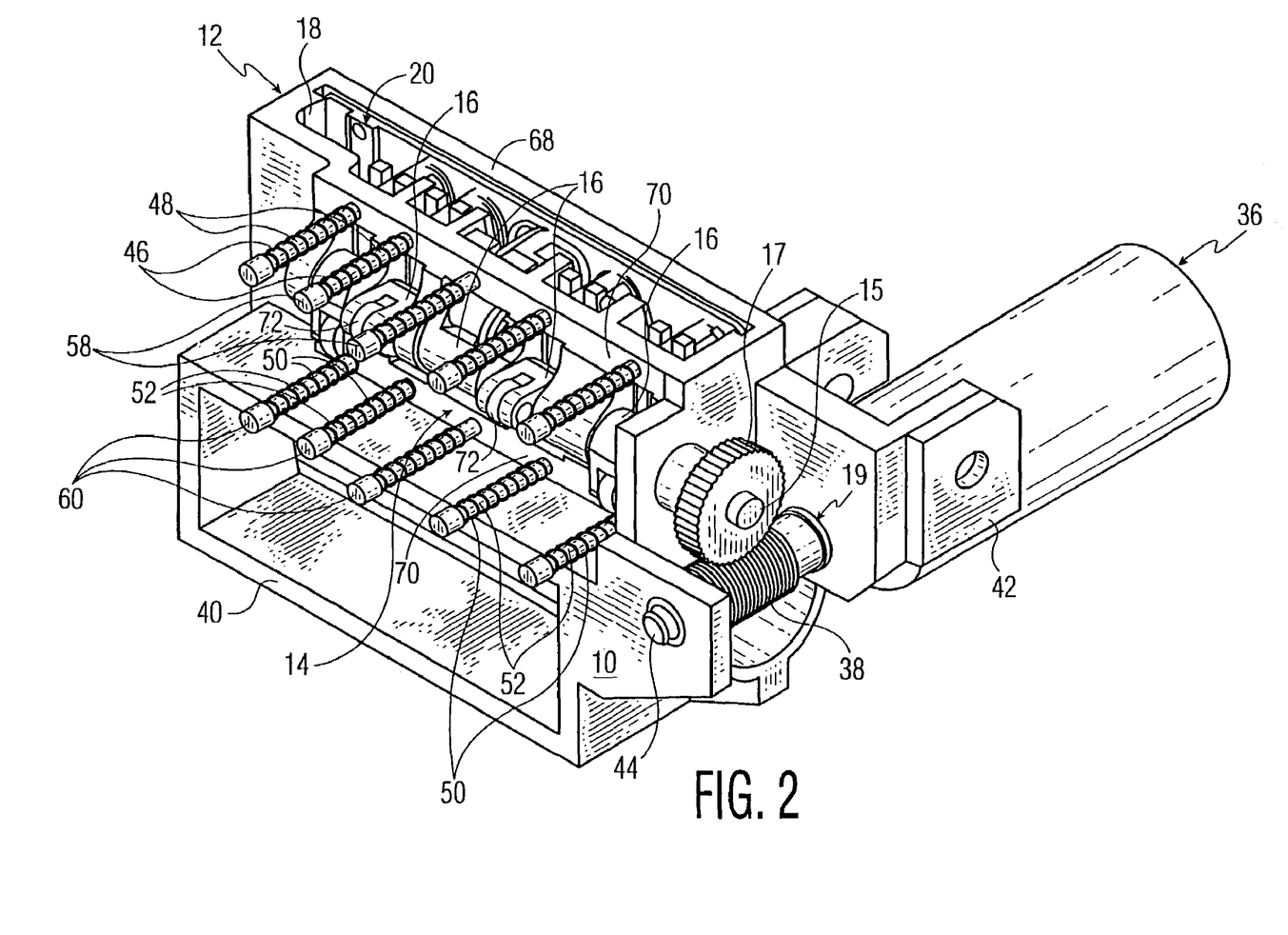
FIG. 2 is a perspective view of an automated ampoule breaking device holding the ampoule-containing substrate of FIG. 1 for one embodiment of the present invention.
Figure 3:
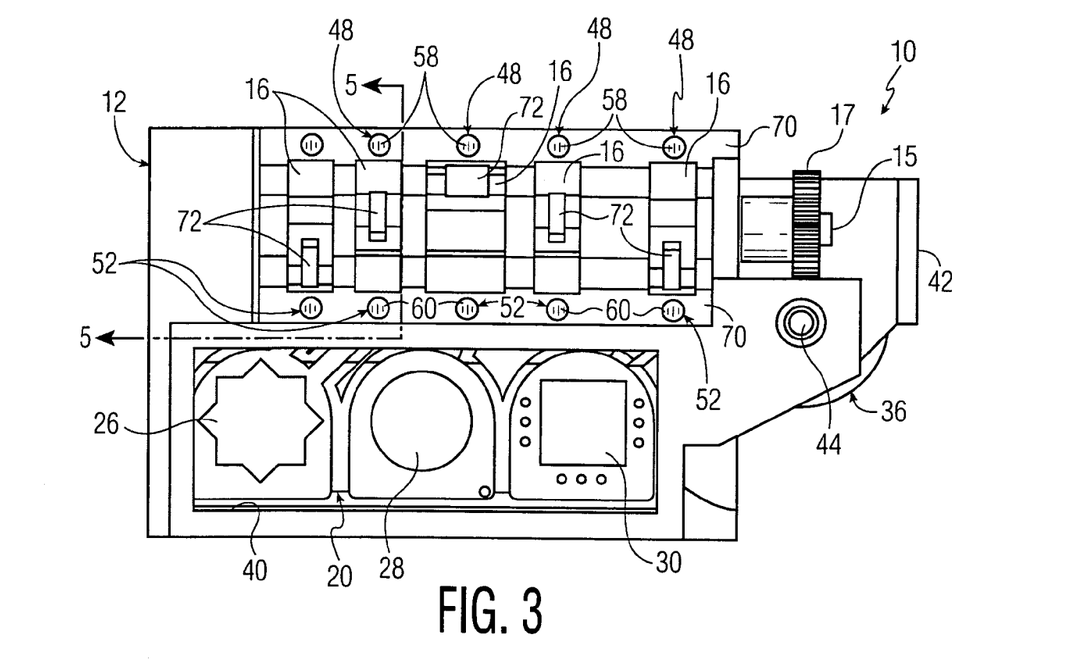
FIG. 3 is front elevation view of the automated ampoule breaking device in accordance with the present invention.

Referring to FIGS. 2 and 3, an automated ampoule breaking device or device identified generally by reference numeral 10 is shown for one embodiment of the present invention. The device 10 of the present invention is constructed to automate the chemical testing method corresponding to the EMT 20 and employs a combination of mechanical and electronic subsystems to implement the test feature of the chemical detection system. The mechanical subsystem is designed to reliably break and completely crush the glass ampoules 25 to release the contents thereof. The mechanical subsystem further ensures that the content released from the crushed ampoules 25 is directed to a desired target location (i.e., test surface) through the channel 32 molded into the substrate 22.

The electronic subsystem is designed to provide the source of energy required to break the glass ampoules 25 and control the precise movements of the mechanical subsystem. The electronic subsystem further automates the operation and eliminates the need for a human user or operator to manually crush the glass ampoules 25 and repetitively squeeze the flexible compartments 24 of the substrate 22 to expel the contents of the crushed glass ampoule 25 onto the test surface 26, 28, and 30.

The device 10 is intended for operation in association with any chemical detection system utilizing ampoule-equipped EMTs that are designed to collect and analyze sample compounds primarily in the vapor or gaseous phase. A suitable example of an EMT-based chemical detection system is the M256 chemical agent detector kit previously described above which provide self-contained point detection of a range of chemical agents. Although the present invention is described for use in context with the EMT 20 forming part of the M256 chemical agent detector kit, it may readily be modified for use and operation with any similar substrates containing ampoules.

The device 10 can be composed of any suitable durable, chemically resistant material capable of withstanding a range of environmental conditions, temperatures and physical forces, and is preferably composed of metal and plastic extruded or molded material. The device 10 can be readily assembled or constructed using commercially available, off-the-shelf components.

The device 10 comprises generally a carriage 12 having a top opening 18 for receiving and securely retaining the EMT 20, a camshaft assembly 14 including a camshaft 15 operatively engaged to a plurality of cams 16 for implementing the ampoule breakage, and a view window 40 extending through the lower end of the carriage 12 for viewing and monitoring the test surfaces 26, 28 and 30 during testing.

The carriage 12 includes a back wall 68 to provide rear support to the EMT 20 in the top opening 18. The device 10 may further include a microprocessor (not shown), a motor 36 controlled by the microprocessor (not shown) through a motor controller (not shown), a worm gear assembly 19 operatively engaged to the camshaft assembly 14 and the motor 36 for efficiently transferring mechanical power supplied by the motor 36 to the camshaft 15. The motor 36 may be selected from any suitable motor capable of rotating at very precise positions or rotating by precise angles, including electric motors such as, for example, a stepper motor, a servomotor, a synchronous motor, and an induction motor, and preferably a stepper motor. The EMT 20 is maintained in the upright position by the device 10 to ensure that the reagents released from the ampoules 25 are free to move downwardly by gravity feed through the channels 32 to the test surfaces 26, 28 and 30 below. Once the test is completed and the results read, the EMT 20 can be removed from the device 10 and discarded, and replaced with a new one.

The carriage 12 further includes a motor mount 42 for retaining the motor 36 in a fixed position. The motor 36 operates to rotatively drive the camshaft 15 via the worm gear assembly 19. The drive shaft 44 of the motor 36 is axially oriented perpendicularly to the camshaft 15. The worm gear assembly 19 includes a worm gear 38 forming part of a drive shaft 44 of the motor 36, and a worm gear 17 forming part of the camshaft 15. Under the power of the motor 36, the worm gear 38 of the drive shaft 44 engages and drives the worm gear 17 of the camshaft 15. The camshaft 15 and the cams 16 rotate in response to the movement of the worm gear assembly 19. The worm gear assembly 19 increases the mechanical torque thus permitting the use of smaller motors of lower weight and power, and thus, decreasing the overall size of the device 10.

The cams 16 are each positioned along the camshaft 15 in front of the flexible compartments 24 with the back wall 68 providing support to the rear side of the substrate 20. Each of the cams 16 may be rotationally positioned offset from one another to facilitate the breaking of ampoules 25 in a predetermined sequence. Each of the cams 16 are adapted to exert a force at a point of their rotational cycles against the substrate 22, and more specifically against the flexible compartment 24 containing the ampoule 25 as will be further described hereinafter.

The cams 16 each include a roller 72 disposed at the end thereof and retained by a pin 78 extending through the projecting portion 16 thereof. The pin 78 facilitates rotation of the roller 72 upon contact with a work surface. The roller 72 operates to substantially reduce friction between the cam 16 and the corresponding flexible compartment 24 and the ampoule 25 and to efficiently and effectively focus the force exerted as will be further described hereinafter. It is preferable that each of the cams 16 moves in a manner where the force exerting portions of the cams 16 sweeps from an upper position to a lower position relative to the ampoule 25. The number, size and timing of the cams 16 may be modified as needed for each application and depending on the configuration and the number, shape and size of the ampoules 25 provided on the substrate.

Each of the cams 16 have associated therewith upper and lower sliding pins 48 and 52 extending through a corresponding sliding mount 70 of the carriage 12. The upper and lower sliding pins 48 and 52 are slidably movable in a reciprocating manner through the sliding mount 70. Each of the upper and lower sliding pins 48 and 52 are operatively engaged to upper and lower springs 46 and 50, respectively, coiled therearound. The upper and lower springs 46 and 50 are maintained under compression by respective stop caps 58 and 60 disposed at the ends of the sliding pins 48 and 52, respectively, and normally biases the respective sliding pins 48 and 52 in the outward direction away from the carriage 12.

Figure 4:
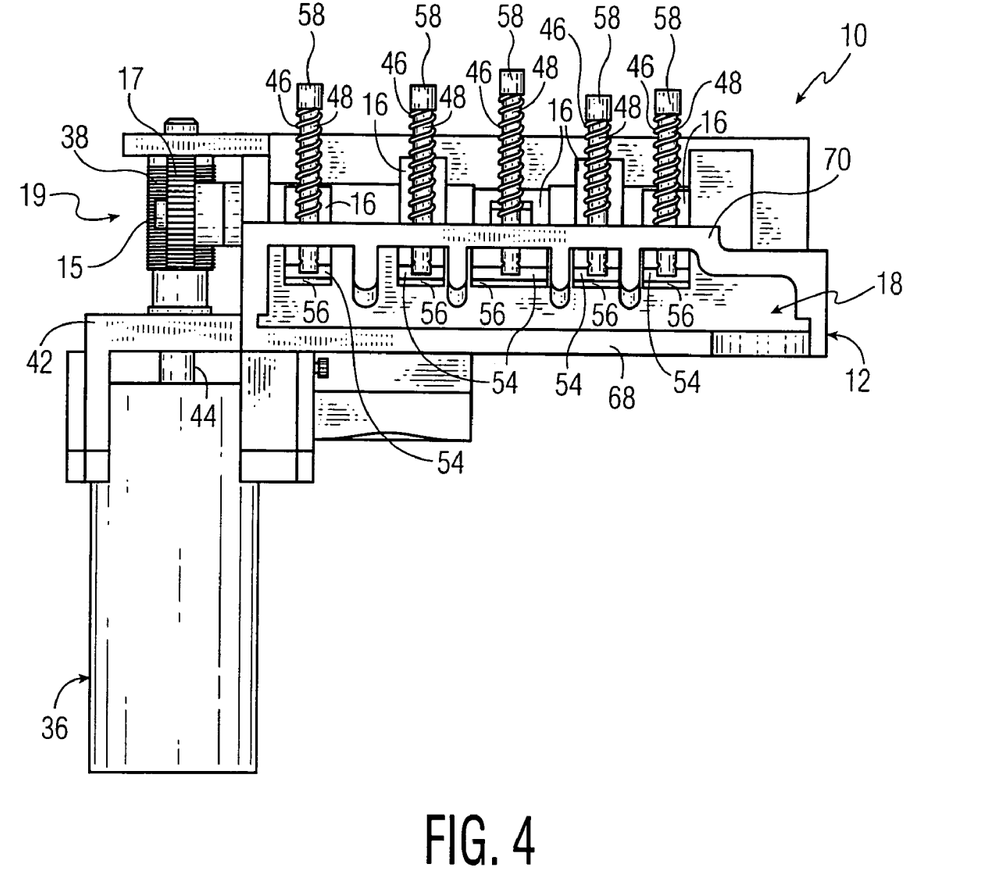
FIG. 4 is a top plan view of the automated ampoule breaking device with the ampoule containing substrate removed from the device in accordance with the present invention.

Referring to FIG. 4, each of corresponding pair of upper and lower sliding pins 48 and 52 (see FIG. 2) extends through their respective sliding mounts 70 of the carriage 12, and are pivotally attached to an impact plate 54. The impact plate 54 moves back and forth in an oscillating motion within the top opening 18 in response to the movement of the respective cam 16. The impact plate 54 is adapted to contact the flexible compartment 24 and crush the ampoule 25 as it moves toward the back wall 68 of the carriage 12. The impact plates 54 each further include a resilient contact surface 56. The resilient contact surface 56 may be composed of a rubber material to yield a pliable texture surface for completely pulverizing the ampoule 25, while exerting consistent pressure to uniformly squeeze the contents of the broken ampoule 25 from the flexible compartment 24 into the channel 32.

The upper and lower springs 46 and 50 of the respective pins 48 and 52 are normally under compression by the stop caps 58 and 60, respectively, and operate to urge the impact plate 54 away from the substrate 22 of the EMT 20 as the cam 16 retreats. During operation, the cams 16 are adapted to rotate and selectively move the respective impact plates 54 toward the back wall 68 and against the corresponding ampoules of the flexible compartments 24 for facilitating breakage at the appropriate times in a predetermined sequence as will be further described hereinafter.

Figure 5:
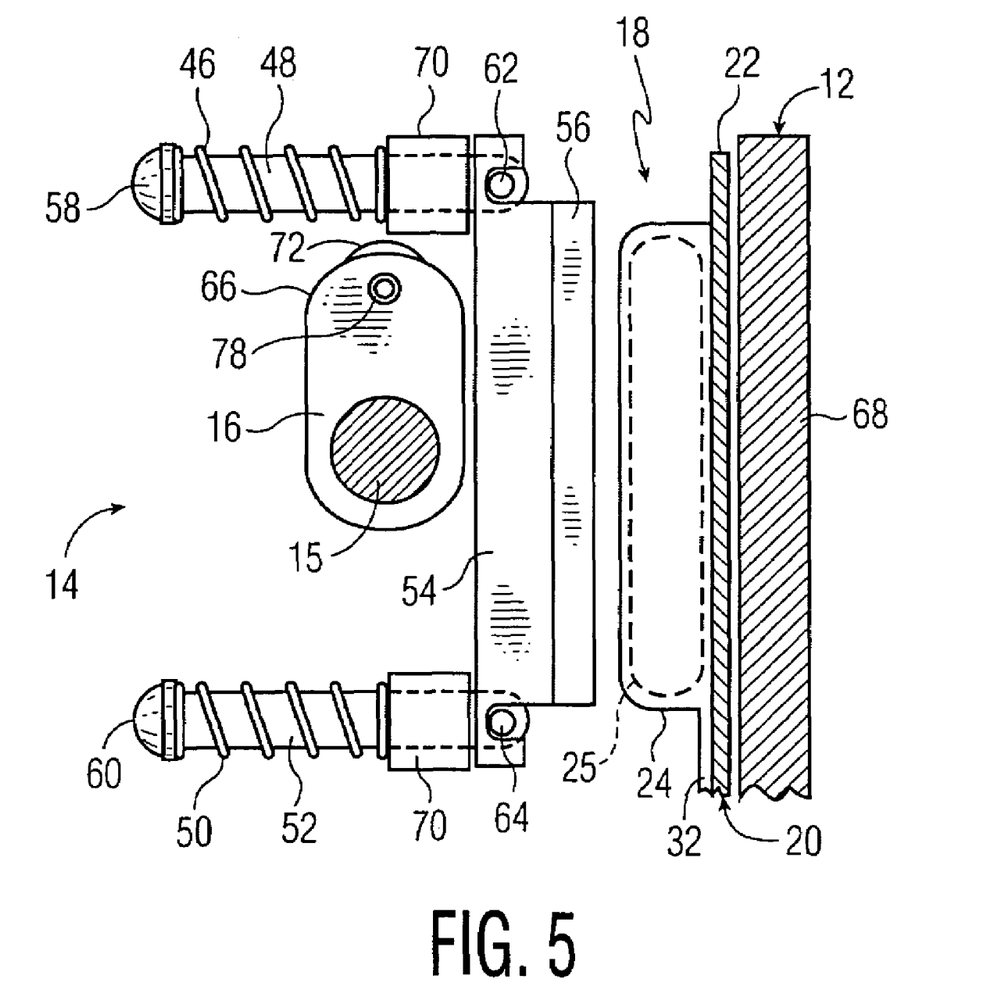
FIG. 5 is a cross-sectional view along lines 5-5 of FIG. 3 illustrating a portion of a camshaft assembly of the automated ampoule breaking device adapted for breaking an ampoule housed in a flexible compartment of the substrate in accordance with the present invention.

Referring to FIG. 5, an ampoule breaking unit forming part of the camshaft assembly 14 is shown in greater detail with the substrate 22 of the EMT 20 occupying the top opening 18 of the carriage 12. The substrate 22 of the EMT 20 includes the ampoule 25 enclosed within the flexible compartment 24, and the channel 32 in fluid communication with the ampoule 25 and the corresponding test surface 26 (see FIG. 1). The rear side of the substrate 22 is positioned flushed against the interior side of the back wall 68 of the carriage 12. The upper and lower sliding pins 48 and 52 are each attached to the upper and lower ends of the impact plate 54 via pivots 62 and 64, respectively. The pivots 62 and 64 provide the impact plate 54 with a greater degree of lateral movement relative to the cam 16 as will be further described hereinafter.

The cam 16 includes a projecting portion 66 rotatable in the clockwise direction in accordance with the movement of the camshaft 15, and the roller 72 extending from the distal end of the projecting portion 66 to reduce frictional resistance with the impact plate 54. The projecting portion 66 may be configured to strike the impact plate 54 at one or more points along its circular path. The cam 16 can be a simple tooth, for example, or an eccentric disc or other shape that produces a smooth oscillating motion in the impact plate 54.

As the projecting portion 66 and roller 72 contacts the impact plate 54, the pivots 62 and 64 allows the upper end of the impact plate 54 to initially move against the upper portion of the ampoule 25 where the resilient contact surface 56 makes initial contact. As the cam 16 rotates further, the projecting portion 66 and roller 72 presses the impact plate 54 and the resilient contact surface 56 against the ampoule 25. This drives the ampoule 25 against the back wall 68 of the carriage 12. The force is applied continuously until the ampoule 24 breaks, and the resilient contact surface 56 is forced against the back wall 68 of the carriage 12, thereby expelling the contents of the ampoule 25 through the channel 32 and out of the flexible compartment 24. Once the cam 16 is rotated through 180 degrees, the impact plate 54 is urged back to the resting position away from the broken ampoule 25 by the upper and lower springs 46 and 50 via the upper and lower sliding pins 48 and 52, respectively.

The camshaft assembly 14 includes the upper and lower springs 46 and 50 at the upper end and the lower end of the impact plate 54. The upper pivot 62 and the lower pivot 64 provide the impact plate 54 with the greater freedom of lateral movement. Furthermore, it is preferable that the upper spring 46 exhibits a lower spring rate than the lower spring 50. This ensures that the initial movement of the impact plate 54 is limited to the upper end thereof until the ampoule 25 is broken. As the upper end of the impact plate 54 contacts the back wall 68, the lower end of the impact plate 54 begins to move against the ampoule 25. The progressive contact by the impact plate 54 forces and directs the contents of the ampoule 25 down the flexible compartment 24 to the channel 32.

Each of the ampoule breaking units of the device 10 can be cascaded together on the camshaft 15, thereby enabling the breakage of multiple ampoules sequentially or en masse simultaneously. The cams 16 can be indexed 90 degrees apart thus permitting the cams 16 to break the ampoules 25 at different times to suitably apportion the force needed to break all the ampoules 25.

As noted previously, each of the cams 16 includes the roller 72 at the projecting portion 66 to reduce the overall force needed to break the ampoules 25 and to reduce the frictional resistance between the cam 16 and the impact plate 54. Additionally, the impact plate 54 may further include a puncture member (not shown) located proximately the upper end thereof. The puncture member (not shown) is adapted to puncture the upper end of the flexible compartment 24 to allow pressure to equalize therein, thus allowing the contents of the ampoule 25 to flow freely from the flexible compartment 24. Although the device 10 of the present embodiment is described to include five ampoule breaking units, the size, indexing and positioning of the cams 16 and the number of ampoule breaking units may be modified depending on several factors including, but not limited to, the particular application requirements, the number and configuration of the ampoules, and the breakage sequence of the ampoules.

The cams 16 are driven by the motor 36 that may be a continuously rotating synchronous motor energized by an AC or DC source, however it is preferably a stepper motor using a single position switch (not shown) to set a home position. The motor 36 is controlled by the microprocessor (not shown) through a motor controller (not shown) for precise control, timing and accuracy. In an alternative embodiment, the motor 36 may be replaced with a manually powered hand crank mechanism attached to the drive shaft 44 for enabling manual hand-powered operation. Alternatively, the hand crank mechanism can be attached directly to the camshaft 15 obviating the need for a worm gear assembly. In this manner, the user can drive the camshaft 15 and the cams 16 to implement the ampoule breaking sequence.

Figure 6:
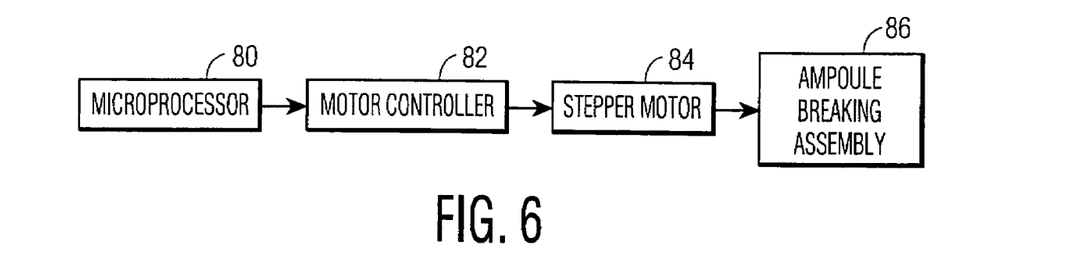
FIG. 6 is a flowchart and block schematic diagram detailing the operation of the automated ampoule breaking device in accordance with the present invention.

Referring to FIG. 6, the device 10 comprises a microprocessor 80, a motor controller 82, a stepper motor 84 and an ampoule breaking assembly 86 forming part of the camshaft assembly 14. When the device 10 is powered up for operation and an EMT 20 is inserted into the top opening 18, the microprocessor 80 sends an initial trigger signal to the motor controller 82. The microprocessor 80 can be activated when an EMT 20 is inserted into the device 10. The motor controller 82 in response to the trigger signal transmits a pulse signal or sequence of pulse signals to the stepper motor 84. This energizes the stepper motor 84 and causes it to rotate in response to each pulse signal a set angle very precisely. The ampoule breaking assembly 86 driven by the stepper motor 84 moves the corresponding cam 16 against the impact plate 54 to crush the ampoule 25 and draw the contents down the channel 32 onto the testing surface 26, 28 or 30. The microprocessor 80 re-initiates the process described above after lapsing of a pre-set time interval. In this manner, the microprocessor 80 allots the appropriate amount of time for the reagents from the broken ampoules 25 to react with the sample on the testing surfaces 26, 28, and 30. The process is thus repeated in a sequential manner for each stage of the ampoule breakage at the appropriate time intervals.

Figure 7:
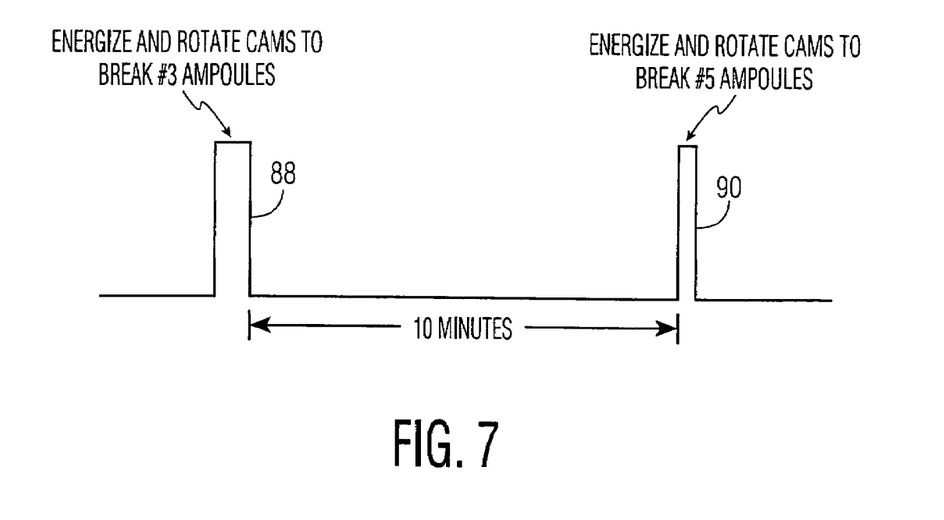
FIG. 7 is a timing diagram for implementing the automated ampoule breaking device in accordance with the present invention.

Referring to FIG. 7, an example of a timing diagram corresponding to the motor 36 of device 10 is shown for illustrating one mode of operation. In this example, the motor controller 82 generates a pulse or pulses 88 to energize the stepper motor 84 and initiates the breaking of the centermost four ampoules 25, generally designated as #3 ampoules in FIG. 7, and directing the contents thereof to associated testing surface 26, 28 or 30. Once any ampoule 25 is broken, the device 10 directs the reagent to an associated one of the test surfaces 26, 28 or 30. The microprocessor 80 monitors the device 10 for about ten minutes and generates another initiating signal 90 to the motor controller 82 to apply pulses to the stepper motor 84 to break the remaining outermost ampoules 25 designated as #5 ampoules in FIG. 7, in this example. The amount of time between pulses may vary depending on the desired sequence for breaking the ampoules 25, which is not limited to the aforesaid example, and is tailored to the particular application. Note that the cams 16 are angularly offset from one another in a manner to provide a desired ampoule breaking sequence.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. An automated ampoule breaking device, comprising:
a carriage having an opening for receiving and securely retaining a substrate in a substantially upright position, said substrate including at least one flexible compartment, each flexible compartment having an upper end, a lower end having an outlet, and at least one ampoule contained therein;
a shaft rotatably engaged to said carriage, said shaft being rotatably driven by a force generating mechanism; and
at least one projection operatively associated with said shaft, wherein said at least one projection is rotatably movable about the axis of the shaft to apply a sufficient force progressively from the upper to the lower end of the corresponding flexible compartment to crush said at least one ampoule and direct the contents of said crushed ampoule out of and through the outlet at the lower end of the respective flexible compartment.

2. The device of claim 1, wherein the projection is in the form of a cam.

3. The device of claim 1, wherein the force generating mechanism is selected from the group consisting of a motor and a manually powered hand-crank mechanism.

4. The device of claim 3, wherein the motor is selected from the group consisting of a stepper motor, a servomotor, a synchronous motor, and an induction motor.

5. The device of claim 4, wherein the motor is a stepper motor.

6. The device of claim 1, further comprising an impact plate operatively associated with and responsive to the position of a corresponding projection, said impact plate adapted for reciprocating movement to transmit force from the projection to the corresponding flexible compartment progressively from the upper to the lower end of said compartment and to crush said at least one ampoule and direct the contents of the ampoule through the outlet at the lower end of said flexible compartment.

7. The device of claim 6, wherein the projection further comprises a roller disposed on the distal end thereof, and adapted for rolling contact with the impact plate to reduce frictional resistance therebetween.

8. The device of claim 6, wherein the impact plate further comprises a resilient contact surface.

9. The device of claim 6, further comprising:
an upper sliding pin and a lower sliding pin slidably mounted through the carriage, said upper and lower sliding pins operatively associated with a corresponding impact plate;
an upper pivot connecting the upper sliding pin to the upper end of the impact plate, and a lower pivot connecting the lower sliding pin to the lower end of the impact plate; and
a spring mechanism operatively associated with the upper and lower sliding pins for normally biasing the impact plate against the projection and away from the substrate.

10. The device of claim 9, wherein the spring mechanism comprises an upper spring coiled around the upper sliding pin, and a lower spring coiled around the lower sliding pin.

11. The device of claim 10, wherein the spring rate of the upper spring is less than the spring rate of the lower spring.

12. The device of claim 1, further comprising at least one piercing element located proximate the upper end of the substrate for puncturing a hole at the upper end of the flexible compartment for facilitating release of the contents of the broken ampoule from the flexible compartment through the outlet at the lower end of said flexible compartment.

13. The device of claim 1, further comprising:
a microprocessor programmed for initiating a sequence of ampoules to be broken by the device, said microprocessor programmed to generate initiating trigger signal at predetermined time intervals; and
a motor controller responsive to the initiating trigger signal which generates an actuation signal to the force generating mechanism to rotate the shaft and said at least one projection by a predetermined amount to break at least one ampoule.

* * * * *